(12) United States Patent
Hassan et al.

(10) Patent No.: US 7,914,744 B2
(45) Date of Patent: *Mar. 29, 2011

(54) METHOD FOR MAKING CHLOROHYDRINS

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: Synfuels International, Inc., Dallas, TX (US)

( * ) Notice: Subject to any disclaimer, the term of this patent is extended or adjusted under 35 U.S.C. 154(b) by 152 days.

This patent is subject to a terminal disclaimer.

(21) Appl. No.: 12/276,968

(22) Filed: Nov. 24, 2008

(65) Prior Publication Data

US 2009/0136396 A1    May 28, 2009

Related U.S. Application Data

(62) Division of application No. 12/143,492, filed on Jun. 20, 2008, now Pat. No. 7,482,496.

(60) Provisional application No. 60/946,487, filed on Jun. 27, 2007.

(51) Int. Cl.
*B01J 10/10* (2006.01)
*B01J 14/00* (2006.01)

(52) U.S. Cl. .......... 422/129; 422/305; 568/844

(58) Field of Classification Search .......... 422/305, 422/129; 568/844
See application file for complete search history.

(56) References Cited

U.S. PATENT DOCUMENTS

| | | | |
|---|---|---|---|
| 5,146,011 A | 9/1992 | Shen et al. | |
| 5,877,350 A | 3/1999 | Langer et al. | |
| 6,051,742 A | 4/2000 | Green et al. | |
| 6,241,472 B1 | 6/2001 | Bosch et al. | |
| 6,368,366 B1 | 4/2002 | Langer et al. | |
| 6,368,367 B1 | 4/2002 | Langer et al. | |
| 6,383,237 B1 | 5/2002 | Langer et al. | |
| 7,157,609 B2 | 1/2007 | Tanaka et al. | |
| 7,461,970 B2 | 12/2008 | Brown | |
| 2004/0052158 A1 | 3/2004 | Holl | |
| 2009/0136392 A1 | 5/2009 | Hassan et al. | |
| 2009/0136393 A1 | 5/2009 | Hassan et al. | |
| 2009/0136395 A1 | 5/2009 | Hassan et al. | |
| 2009/0323458 A1 | 12/2009 | Fischer et al. | |

OTHER PUBLICATIONS

International Search Report, International Application No. PCT/US2008/068168, dated Jan. 8, 2009.
USPTO Office Action Dated Jun. 25, 2010 for U.S. Appl. No. 12/276,968.
USPTO Office Action Dated Apr. 20, 2010 for U.S. Appl. No. 12/411,660.
USPTO Office Action Dated Apr. 20, 2010 for U.S. Appl. No. 12/427,286.
USPTO Office Action Dated Apr. 23, 2010 for U.S. Appl. No. 12/568,155.
USPTO Office Action Dated Apr. 27, 2010 for U.S. Appl. No. 12/568,280.
USPTO Office Action Dated May 5, 2010 for U.S. Appl. No. 12/142,120.
USPTO Office Action Dated Jun. 25, 2009 for U.S. Appl. No. 12/142,447.
USPTO Office Action Dated Jan. 7, 2010 for U.S. Appl. No. 12/142,447.
USPTO Office Action Dated May 13, 2010 for U.S. Appl. No. 12/142,447.
USPTO Office Action Dated Feb. 4, 2010 for U.S. Appl. No. 12/492,721.
USPTO Office Action Dated Feb. 18, 2010 for U.S. Appl. No. 12/635,433.
USPTO Office Action Dated Feb. 18, 2010 for U.S. Appl. No. 12/635,454.
USPTO Office Action Dated May 14, 2010 for U.S. Appl. No. 12/137,441.
USPTO Office Action Dated Feb. 19, 2010 for U.S. Appl. No. 12/144,459.
USPTO Office Action Dated Sep. 2, 2009 for U.S. Appl. No. 12/142,433.
USPTO Office Action Dated Jan. 29, 2010 for U.S. Appl. No. 12/142,433.
USPTO Office Action Dated May 24, 2010 for U.S. Appl. No. 12/142,433.
USPTO Office Action Dated Apr. 30, 2010 for U.S. Appl. No. 12/141,191.
USPTO Office Action Dated Oct. 27, 2009 for U.S. Appl. No. 12/142,120.
USPTO Office Action Dated May 5, 2010 for U.S. Appl. No. 12/571,537.
Office Action Dated Jul. 28, 2010 for U.S. Appl. No. 12/635,433.

*Primary Examiner* — Elvis O Price
(74) *Attorney, Agent, or Firm* — Porter Hedges LLP; Timothy S. Westby

(57) ABSTRACT

Methods and systems for the preparation of chlorohydrins are described herein. The methods and systems incorporate the novel use of a high shear device to promote dispersion and solubility of olefins into the chlorinating phase. The high shear device may allow for lower reaction temperatures and pressures and may also reduce chlorination time.

10 Claims, 2 Drawing Sheets

METHOD FOR MAKING CHLOROHYDRINS

CROSS-REFERENCE TO RELATED APPLICATIONS

This application is a divisional application of U.S. patent application Ser. No. 12/143,492, filed Jun. 20, 2008, which claims the benefit under 35 U.S.C. §119(e) of U.S. Provisional Patent Application No. 60/946,487, filed Jun. 27, 2007. The disclosure of said applications are hereby incorporated herein by reference.

STATEMENT REGARDING FEDERALLY SPONSORED RESEARCH OR DEVELOPMENT

Not Applicable.

BACKGROUND

1. Field of the Invention

This invention relates generally to the field of chemical reactions. More specifically, the invention relates to methods of making chlorohydrins incorporating high shear mixing.

2. Background of the Invention

Chlorohydrins are useful as intermediates in producing various compounds. For example, propylene chlorohydrin and butylene chlorohydrin are used in producing propylene oxide and butylene oxide, respectively.

Various processes are known for the production of chlorohydrins. For example, olefin chlorohydrins are typically prepared by reacting an olefin with chlorine in the presence of water. This process is believed to occur by means of an intermediate cyclic chloronium ion which reacts with the water to form an olefin chlorohydrin. The olefin may be one containing from 8 to about 30 carbon atoms. However, the process also concurrently forms undesirable dichloride byproducts when aqueous chloride ions react with the cyclic chloronium ions. Significant yield losses are typically suffered and the byproducts must be separated from the desired olefin chlorohydrin, an operation that adds to the cost of making the chlorohydrin. Alternatively, the process described above may include a water immiscible solvent. Therefore, the reaction would entail the addition of hypochlorous acid to a long chain olefin in the presence of water in a water immiscible solvent. Suitable solvents include decane, chloroform and petroleum ether.

Other processes for producing chlorohydrins involve reacting olefins with hypochlorous acid, wherein the process requires preliminarily acidifying the olefin with gaseous hydrochloric acid and carrying out the process at a pH of between 2 to 7, and preferably between 5 to 6. Another method of making chlorohydrins involves preparing hypochlorous acid by reacting chlorine and water in the presence of alkaline earth metal hydroxides (maintaining a pH below 7.0), then, reacting the hypochlorous acid mixture with a vinyl group-containing compound. Alternatively the preparation of chlorohydrin may be achieved by reaction of olephins with trichloroisocyanuric acid in alcohols, acetic acid or aqueous acetone.

Various other methods of forming chlorohydrins are also well known such as reacting olefins with t-butyl hypochlorite or hypochlorous acid substantially free of chloride ions. However, these methods typically either result in the production of numerous byproducts or require various, costly processing steps or long reaction times, thus hindering the commercial viability of the methods. For these reasons, there remains a need for a process for producing chlorohydrin that is effective and results in high yields of the desired product.

In light of the above, it is apparent that research has been focused on different reaction pathways in producing chlorohydrins. However, none of these methods discuss improving the solubility and mass transfer of the reactants through improved mixing.

Consequently, there is a need for accelerated methods for making chlorohydrins by improving the mixing of olefins into the liquid chlorinating phase.

BRIEF SUMMARY

Methods and systems for the preparation of chlorohydrins are described herein. The methods and systems incorporate the novel use of a high shear device to promote dispersion and solubility of olefins into the chlorinating phase. The high shear device may allow for lower reaction temperatures and pressures and may also reduce chlorination time. Further advantages and aspects of the disclosed methods and system are described below.

In an embodiment, a method of making a chlorohydrin comprises contacting an olefin with a chlorinating agent. In an embodiment the liquid is an aqueous solution, a hypochlorous acid solution, an aqueous hypochlorite solution or chlorine dissolved in $H_2O$ and the gas comprised of an olefin which is reactive under the conditions of mixing with one or more components of the liquid to form reaction products including the desired olefin chlorohydrin product. The method also comprises flowing the olefin and the chorinating agent through a high shear device so as to form dispersion with bubbles less than about 1 μm and form a chlorohydrin.

In an embodiment, a system for making a chlorohydrin comprises at least one high shear device configured for chlorinating an olefin. The high shear device comprises a rotor and a stator. The rotor and the stator are separated by a shear gap in the range of from about 0.02 mm to about 5 mm. The shear gap is a minimum distance between the rotor and the stator. The high shear device is capable of producing a tip speed of the at least one rotor of greater than about 23 m/s (4,500 ft/min). In addition, the system comprises a pump configured for delivering a liquid stream comprising liquid phase to the high shear device.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Figure 1:
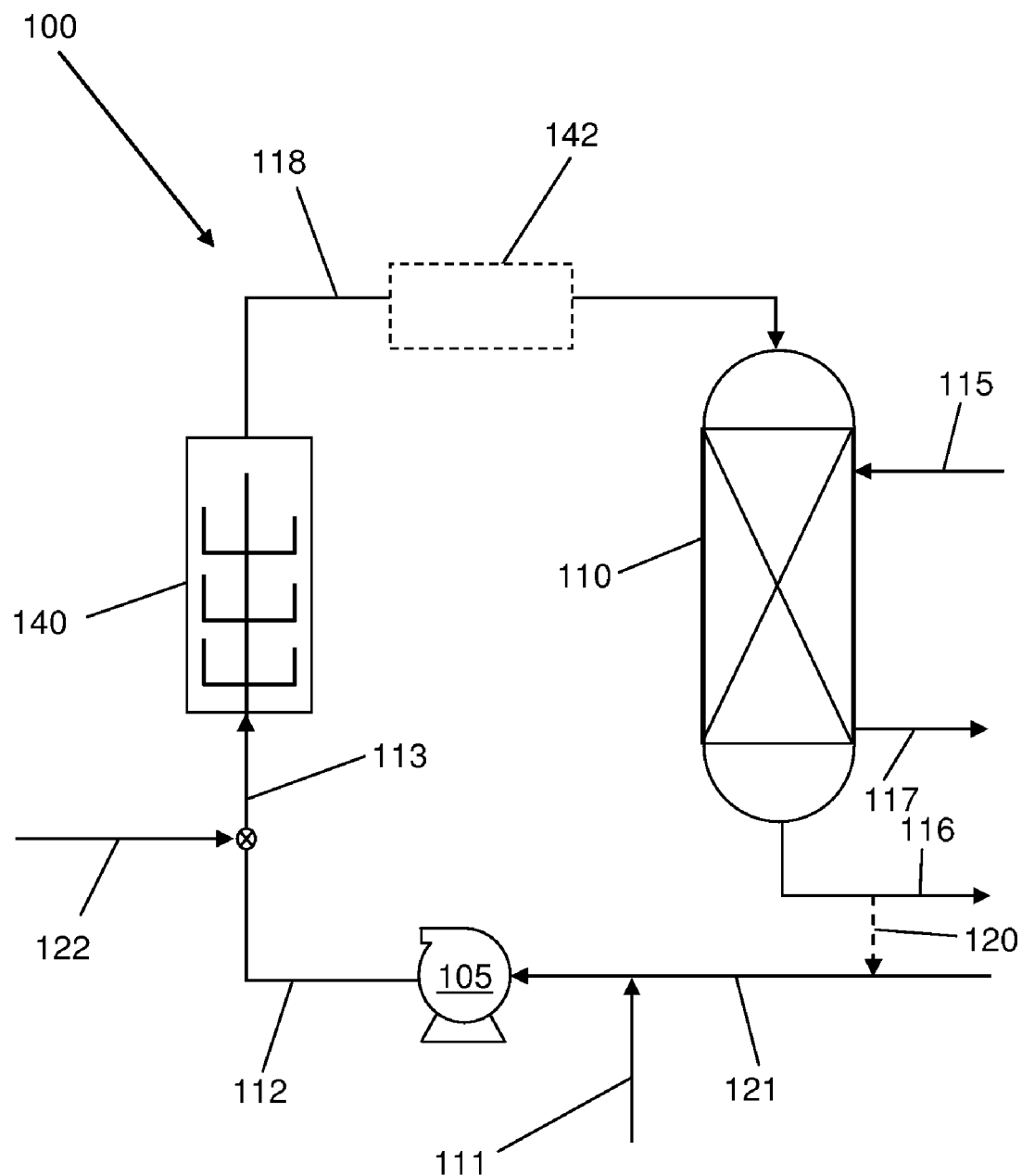
FIG. 1 illustrates a general flow diagram of an embodiment of a process of making chlorohydrins using a high shear device.

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ".

DETAILED DESCRIPTION OF THE PREFERRED EMBODIMENTS

The disclosed methods and systems for the chlorination of an olefin employ a high shear mechanical device to provide rapid contact and mixing of the olefin gas and chlorinating agent in a controlled environment in the reactor/mixer device. The term "olefin gas" as used herein includes both substantially olefin gas as well as gaseous mixtures containing olefin. In particular, embodiments of the systems and methods may be used in the production of chlorohydrins from the chlorination of olefins in water. Preferably, the method comprises a heterogeneous phase reaction of a chlorine species in liquid phase with an olefin gas. The high shear device reduces the mass transfer limitations on the reaction and thus increases the overall reaction rate.

Chemical reactions involving liquids, gases and solids rely on the laws of kinetics that involve time, temperature, and pressure to define the rate of reactions. In cases where it is desirable to react two (or more) raw materials of different phases (e.g. solid and liquid; liquid and gas; solid, liquid and gas), one of the limiting factors in controlling the rate of reaction involves the contact time of the reactants. As used herein, "multi-phase" refers to a reaction involving reactions with two or more different phases. In the case of heterogeneously catalyzed reactions there is the additional rate limiting factor of having the reacted products removed from the surface of the catalyst to enable the catalyst to catalyze further reactants.

The chlorination of olefins to produce chlorohydrin is a multiphase reaction. During the multiphase reaction, the phases separate spontaneously. The presently disclosed method and system whereby the two phases are intimately mixed to form an emulsion enhances contact surface between the reaction components, thus enhancing the reaction.

The pH of the reaction may have a direct impact on the reaction rate and thus the olefin conversion. The pH employed may vary depending on the chlorines present in the aqueous phase. The maximum pH is about 8. When the aqueous phase contains free chloride ions and molecular chlorine, the pH should not be below 4.5. When an essentially chloride and chlorine-free aqueous solution is employed herein, the pH can range as low as 1. The process described here in comprises an aqueous phase having a pH ranging from about 2 to about 8. Chlorohydrin yield is particularly good in low olefin conversion when an aqueous phase of pH of about 6 is employed.

In conventional reactors, contact time for the reactants and/or catalyst is often controlled by mixing which provides contact with two or more reactants involved in a chemical reaction. Embodiments of the disclosed method comprise an external high shear device to decrease mass transfer limitations and thereby more closely approach kinetic limitations. When reaction rates are accelerated, residence times may be decreased, thereby increasing obtainable throughput. Alternatively, where the current yield is acceptable, decreasing the required residence time allows for the use of lower temperatures and/or pressures than conventional processes. Furthermore, in homogeneous reactions, the disclosed process could be used to provide for uniform temperature distribution within the reactor thereby minimizing potential side reactions.

System for Production of Chlorohydrin. A high shear chlorohydrin production system will now be described in relation to FIG. 1, which is a process flow diagram of an embodiment of a high shear system (HSS) 100 for the production of chlorohydrin via reacting a chlorinating agent with olefins in a gas-liquid phase reaction. The basic components of a representative system include external high shear device (HSD) 140, vessel 110, pump 105 and fluidized or fixed bed 142. As shown in FIG. 1, the high shear device is located external to vessel/reactor 110. Each of these components is further described in more detail below. Line 121 is connected to pump 105 for introducing reactant. Line 113 connects pump 105 to HSD 140, line 118 connects HSD 140 to fluidized or fixed bed 142 and line 119 connects bed to vessel 110. Line 122 is connected to line 113 for introducing an oxygen-containing gas (e.g., $O_2$ or air). Line 117 is connected to vessel 110 for removal of unreacted vapor, and other reaction gases. High shear devices (HSDs) such as a high shear device, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 microns. High shear mechanical devices include homogenizers as well as colloid mills.

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 µm to about 1 µm. At the other end of the spectrum are high shear mixer systems classified as low energy devices. These systems usually have paddles or fluid rotors that turn at high speed in a reservoir of fluid to be processed, which in many of the more common applications is a food product. These systems are usually used when average particle, or bubble, sizes of greater than 20 microns are acceptable in the processed fluid.

Between low energy-high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 µm to about 25 µm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

An approximation of energy input into the fluid (kW/L/min) can be made by measuring the motor energy (kW) and fluid output (L/min). In embodiments, the energy expenditure of a high shear device is greater than 1000 W/m$^3$. In embodiments, the energy expenditure is in the range of from about 3000 W/m$^3$ to about 7500 W/m$^3$. The shear rate generated in a high shear device may be greater than 20,000 s$^{-1}$. In embodiments, the shear rate generated is in the range of from 20,000 s$^{-1}$ to 100,000 s$^{-1}$.

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation V (m/sec) $=\pi \cdot D \cdot n$, where V is the tip speed, D is the diameter of the rotor, in meters, and n is the rotational speed of the rotor, in revolutions per second. Tip speed is thus a function of the rotor diameter and the rotation rate. Also, tip speed may be calculated by multiplying the circumferential distance transcribed by the rotor tip, $2\pi R$, where R is the radius of the rotor (meters, for example) times the frequency of revolution (for example revolutions (meters, for example) times the frequency of revolution (for example revolutions per minute, rpm).

For colloid mills, typical tip speeds are in excess of 23 m/sec (4500 ft/min) and can exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least about 1034 MPa (about 150,000 psi).

Figure 2:
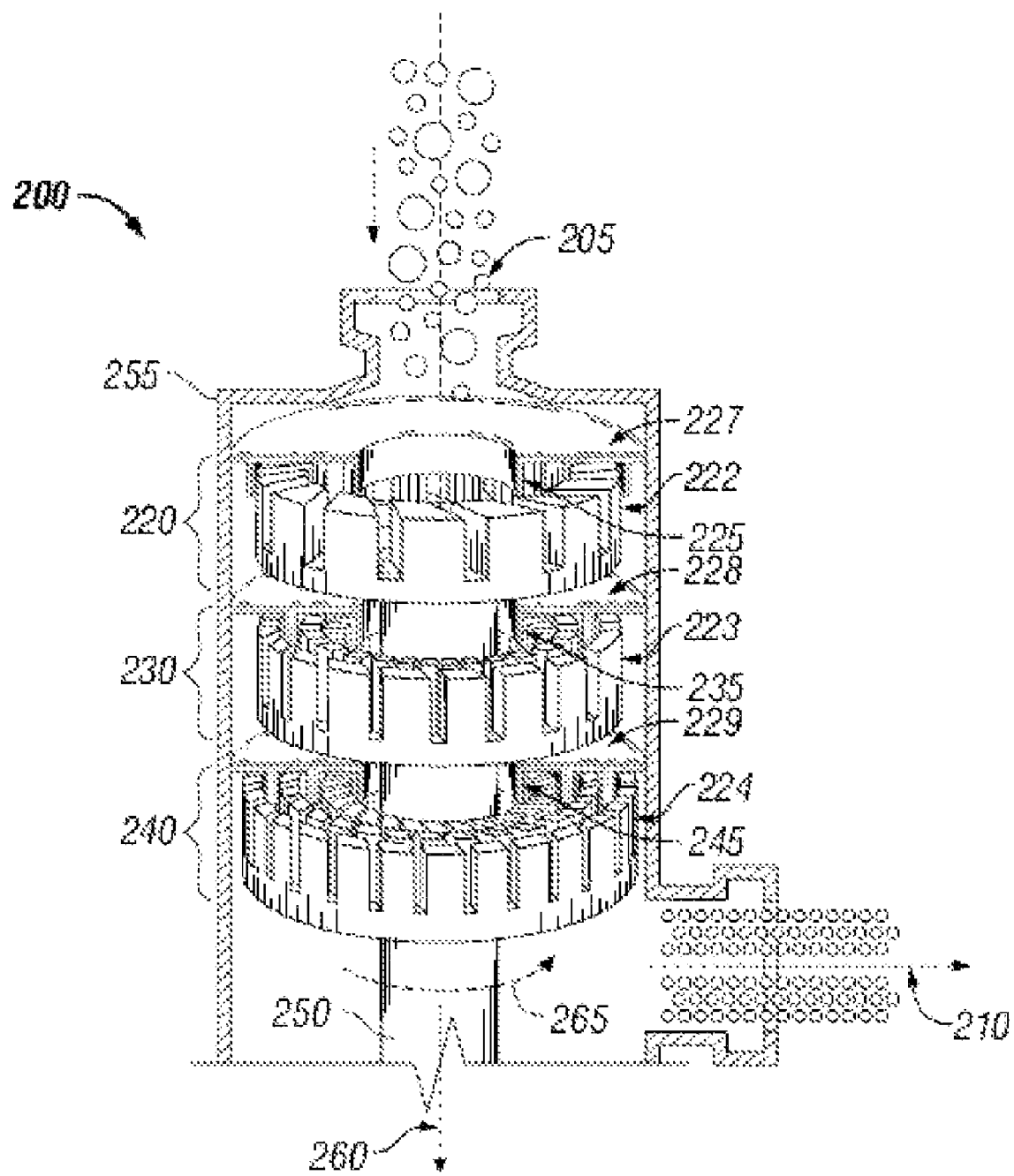
FIG. 2 illustrates a longitudinal cross-section view of a multi-stage high shear device, as employed in an embodiment of the system of FIG. 1.

Referring now to FIG. 2, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. The rotor and the stator may be of any suitable size. In one embodiment, the inner diameter of the rotor is about 64 mm and the outer diameter of the stator is about 60 mm. In further embodiments, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 μm; preferably the bubbles are sub-micron in diameter. In certain instances, the average bubble size is in the range from about 1.0 μm to about 0.1 µm. Alternatively, the average bubble size is less than about 400 nm (0.4 µm) and most preferably less than about 100 nm (0.1 µm).

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 µm in diameter may comprise a micro-foam. Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor (ARR). The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a Dispax Reactor® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min). Several alternative models are available having various inlet/outlet connections, horsepower, nominal tip speeds, output rpm, and nominal flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming).

Vessel. Vessel or reactor 110 is any type of vessel in which a multiphase reaction can be propagated to carry out the above-described conversion reaction(s). For instance, a continuous or semi-continuous stirred tank reactor, or one or more batch reactors may be employed in series or in parallel. In some applications vessel 110 may be a tower reactor, and in others a tubular reactor or multi-tubular reactor. A catalyst inlet line 115 may be connected to vessel 110 for receiving a catalyst solution or slurry during operation of the system.

Vessel 110 may include one or more of the following components: stirring system, heating and/or cooling capabilities, pressure measurement instrumentation, temperature measurement instrumentation, one or more injection points, and level regulator (not shown), as are known in the art of reaction vessel design. For example, a stirring system may include a motor driven mixer. A heating and/or cooling apparatus may comprise, for example, a heat exchanger. Alternatively, as much of the conversion reaction may occur within HSD 140 in some embodiments, vessel 110 may serve primarily as a storage vessel in some cases.

Heat Transfer Devices. In addition to the above-mentioned heating/cooling capabilities of vessel 110, other external or internal heat transfer devices for heating or cooling a process stream are also contemplated in variations of the embodiments illustrated in FIG. 1. Some suitable locations for one or more such heat transfer devices are between pump 105 and HSD 140, between HSD 140 and vessel 110, and between vessel 110 and pump 105 when system 100 is operated in multi-pass mode. Some non-limiting examples of such heat transfer devices are shell, tube, plate, and coil heat exchangers, as are known in the art.

Pumps. Pump 105 is configured for either continuous or semi-continuous operation, and may be any suitable pumping device that is capable of providing greater than 2 atm pressure, preferably greater than 3 atm pressure, to allow controlled flow through HSD 140 and system 100. For example, a Roper Type 1 gear pump, Roper Pump Company (Commerce Ga.) Dayton Pressure Booster Pump Model 2P372E, Dayton Electric Co (Niles, Ill.) is one suitable pump. Preferably, all contact parts of pump 105 are stainless steel, for example, 316 stainless steel. In embodiments, for example, wherein corrosive substances will be pumped (e.g. sulfuric acid) it may be desirable to have gold plated contact surfaces. In some embodiments of the system, pump 105 is capable of pressures greater than about 20 atm. In addition to pump 105, one or more additional, high pressure pump (not shown) may be included in the system illustrated in FIG. 1. For example, a booster pump, which may be similar to pump 105, may be included between HSD 140 and vessel 110 for boosting the pressure into vessel 110.

Production of Chorohydrins. In operation for the chlorination of olefins, respectively, a dispersible olefin gas stream is introduced into system 100 via line 122, and combined in line 113 with a liquid stream to form a gas-liquid stream. The liquid stream includes a chlorinating agent in aqueous phase (i.e. $Cl_2$ dissolved in water). Alternatively, the olefin gas may be fed directly into HSD 140, instead of being combined with the liquid reactant (i.e., water) in line 113. Pump 105 is operated to pump the liquid reactant (water) through line 121, and to build pressure and feed HSD 140, providing a controlled flow throughout high shear (HSD) 140 and high shear system 100. Optionally, a gaseous chlorinating agent such as chlorine gas may be fed into line 121 through line 111. In such an embodiment, an additional high shear device may be incorporated to dissolve the gaseous chlorinating agent into solution.

In a preferred embodiment, olefin gas 122 may continuously be fed into the liquid stream 112 to form high shear feed stream 113 (e.g. gas-liquid stream). In high shear device 140, liquid (i.e. water), chlorinating agent, and the olefin vapor are highly dispersed such that nanobubbles and/or microbubbles of olefin are formed for superior dissolution of olefin vapor into solution. Once dispersed, the dispersion may exit high shear device 140 at high shear outlet line 118. Stream 118 may optionally enter fluidized or fixed bed 142 in lieu of a slurry catalyst process. However, in a slurry catalyst embodiment, high shear outlet stream 118 may directly enter hydration reactor 110 for hydration. The reaction stream may be maintained at the specified reaction temperature, using cooling coils in the reactor 110 to maintain reaction temperature. Chlorination products (e.g. chlorohydrins) may be withdrawn at product stream 116.

In an exemplary embodiment, the high shear device comprises a commercial disperser such as IKA® model DR 2000/4, a high shear, three stage dispersing device configured with three rotors in combination with stators, aligned in series. The disperser is used to create the dispersion of olefins in the liquid medium comprising water (i.e., "the reactants"). The rotor/stator sets may be configured as illustrated in FIG. 2, for example. The combined reactants enter the high shear device via line 113 and enter a first stage rotor/stator combination having circumferentially spaced first stage shear openings. The coarse dispersion exiting the first stage enters the second rotor/stator stage, which has second stage shear openings. The reduced bubble-size dispersion emerging from the second stage enters the third stage rotor/stator combination having third stage shear openings. The dispersion exits the high shear device via line 118. In some embodiments, the shear rate increases stepwise longitudinally along the direction of the flow. For example, in some embodiments, the shear rate in the first rotor/stator stage is greater than the shear rate in subsequent stage(s). In other embodiments, the shear rate is substantially constant along the direction of the flow, with the stage or stages being the same. If the high shear device includes a PTFE seal, for example, the seal may be cooled using any suitable technique that is known in the art. For example, the reactant stream flowing in line 113 may be used to cool the seal and in so doing be preheated as desired prior to entering the high shear device.

The rotor of HSD 140 is set to rotate at a speed commensurate with the diameter of the rotor and the desired tip speed. As described above, the high shear device (e.g., colloid mill) has either a fixed clearance between the stator and rotor or has adjustable clearance. HSD 140 serves to intimately mix the olefin vapor and the reactant liquid (i.e., water). In some embodiments of the process, the transport resistance of the reactants is reduced by operation of the high shear device such that the velocity of the reaction (i.e. reaction rate) is increased by greater than a factor of about 5. In some embodiments, the velocity of the reaction is increased by at least a factor of 10. In some embodiments, the velocity is increased by a factor in the range of about 10 to about 100 fold. In some embodiments, HSD 140 delivers at least 300 L/h with a power consumption of 1.5 kW at a nominal tip speed of at least 4500 ft/min, and which may exceed 7900 ft/min (140 m/sec). Although measurement of instantaneous temperature and pressure at the tip of a rotating shear unit or revolving element in HSD 140 is difficult, it is estimated that the localized temperature seen by the intimately mixed reactants may be in excess of 500° C. and at pressures in excess of 500 kg/cm$^2$ under high shear conditions. The high shear results in dispersion of the olefin gas in micron or submicron-sized bubbles. In some embodiments, the resultant dispersion has an average bubble size less than about 1.5 μm. Accordingly, the dispersion exiting HSD 140 via line 118 comprises micron and/or submicron-sized gas bubbles. In some embodiments, the mean bubble size is in the range of about 0.4 μm to about 1.5 μm. In some embodiments, the mean bubble size is less than about 400 nm, and may be about 100 nm in some cases. In many embodiments, the microbubble dispersion is able to remain dispersed at atmospheric pressure for at least 15 minutes.

Once dispersed, the resulting olefin/chlorinating agent/water dispersion exits HSD 140 via line 118 and feeds into vessel 110, as illustrated in FIG. 1. As a result of the intimate mixing of the reactants prior to entering vessel 110, a significant portion of the chemical reaction may take place in HSD 140, with or without the presence of a catalyst. Accordingly, in some embodiments, reactor/vessel 110 may be used primarily for heating and separation of volatile reaction products from the chlorohydrin product. Alternatively, or additionally, vessel 110 may serve as a primary reaction vessel where most of the chlorohydrin product is produced. Vessel/reactor 110 may be operated in either continuous or semi-continuous flow mode, or it may be operated in batch mode. The contents of vessel 110 may be maintained at a specified reaction temperature using heating and/or cooling capabilities (e.g., cooling coils) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents are stirred continuously or semi-continuously.

Embodiments of the process generally comprise contacting a chlorine source with an olefin under conditions sufficient to form a chlorohydrin. The chlorine source or chlorinating agent may be any source of chlorine that is capable of forming a chlorinating species. Examples of such chlorine sources are chlorine ($Cl_2$), hypochlorous acid (HOCl), chlorine monoxide ($Cl_2O$), or a hypochlorite (—OCl) of an alkali metal or alkaline earth metal. The chlorine source is preferably $Cl_2$, more preferably, $Cl_2$ gas. The chlorinating species may also comprise at least one compound selected from the group consisting of hypochlorous acid, alkali metal hypohalites, and alkaline earth metal hypohalites. Preferably, chlorine source or chlorinating agent is in an aqueous or liquid phase. In on embodiment, the chlorine source or agent may be dissolved in water.

In an embodiment, the method may comprise contacting the chlorinating species with at least one unsaturated organic compound containing from 2 to 10 carbon atoms, preferably 2 to 8 carbons, and more preferably 2 to 6 carbons. The unsaturated organic compound may be selected from the group consisting of substituted and unsubstituted olefins and cyclic olefins. The substituted olefins may have substituents selected from the group consisting of an alkyl radical, a phenyl radical and an alkylphenyl radical (i.e. tolyl, xylyl or ethylphenyl). Each of these radicals may also be unsubstituted or substituted. When substituted, the substituents preferably comprise halides, hydroxides, or inert substituents. By "inert substituents" it is meant that the substituents do not interfere with the process of this invention. Any suitable unsaturated compound containing from 2 to 10 carbon atoms and meeting the criteria specified above can be used in the process of the invention to prepare the corresponding chlorohydrin. Such unsaturated organic compounds include, but are not limited to, ethylene, propylene, butylene, hexene, cyclohexene, cyclopentene, cyclooctene, and mixtures thereof. Examples of substituted olefins include allyl alcohol, allyl chloride, styrene, 4-bromo-1-butene, 3-chloro-1-butene, 3-chloro-2-methylpropene, 1-hexene-3-ol, 3-butene-2-ol, 3-pentene-2-ol, 1-octene-3-ol, and mixtures thereof.

The reaction may proceed under temperature and pressure conditions commonly employed in such catalytic chlorination reactions. Generally, embodiments of the process are carried out by reacting a olefin containing about 1 to about 10 carbon atoms with a chlorine source to obtain the desired chlorohydrin reaction product. More specifically, the chlorination reaction in reactor 110 may be conducted with mixing and at a temperature between 0° C. to 100° C. and pressure between ambient to 100 psig (791 kPa). Preferably, the temperature is from 20° C. to 80° C., more preferably from 40° C. to 60° C.

Multiple Pass Operation. In the embodiment shown in FIG. 1, the system is configured for single pass operation, wherein the output from vessel 110 goes directly to further processing for recovery of chlorohydrin product. In some embodiments it may be desirable to pass the contents of vessel 110, or a liquid fraction containing unreacted olefin, through HSD 140 during a second pass. In this case, line 116 is connected to line 121 via dotted line 120, and the recycle stream from vessel 110 is pumped by pump 105 into line 113 and thence into HSD 140. Additional olefin gas may be injected via line 122 into line 113, or it may be added directly into the high shear device (not shown).

Multiple High shear Devices. In some embodiments, two or more high shear devices like HSD 140, or configured differently, are aligned in series, and are used to further enhance the reaction. Their operation may be in either batch or continuous mode. In some instances in which a single pass or "once through" process is desired, the use of multiple high shear devices in series may also be advantageous. In some embodiments where multiple high shear devices are operated in series, vessel 110 may be omitted. In some embodiments, multiple high shear devices 140 are operated in parallel, and the outlet dispersions therefrom are introduced into one or more vessel 110.

While the preferred embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A system for production of chlorohydrin comprising;
   at least one high shear device configured for chlorinating an olefin, said high shear device comprising a rotor and a stator, said rotor and said stator are separated by a shear gap in the range of from about 0.02 mm to about 5 mm, wherein the shear gap is a minimum distance between said rotor and said stator, and wherein the high shear device is capable of producing a tip speed of the at least one rotor of greater than about 23 m/s (4,500 ft/min);
   a pump configured for delivering a liquid stream comprising liquid phase to the high shear device; and
   a vessel configured for receiving the dispersion from the high shear device and for maintaining a predetermined pressure and temperature.

2. The system of claim 1 wherein the high shear device comprises two or more rotors and two or more stators.

3. The system of claim 1 wherein said high shear device comprises a rotor tip and said device is configured for operating at a flow rate of at least 300 L/h at a tip speed of at least about 23 m/sec.

4. The system of claim 1 wherein said high shear device is configured to provide an energy expenditure greater than about 1000 W/m$^3$.

5. The system of claim 1 wherein the at least one high shear device is configured for producing a dispersion of olefin gas bubbles in a liquid phase comprising and a chlorinating agent, wherein the dispersion has a mean bubble diameter of less than 400 nm.

6. The system of claim 1 comprising at least two high shear devices.

7. The system of claim 1 wherein the high shear device has a tip speed of greater than about 20 m/s (4000 ft/min).

8. The system of claim 1 further comprising a fixed bed reactor, the reactor comprising a chlorination catalyst.

9. The system of claim 1 wherein the high shear device comprises at least two generators.

10. The system of claim 9 wherein the shear rate provided by one generator is greater than the shear rate provided by another generator.

* * * * *

UNITED STATES PATENT AND TRADEMARK OFFICE
CERTIFICATE OF CORRECTION

| | | |
|---|---|---|
| PATENT NO. | : 7,914,744 B2 | |
| APPLICATION NO. | : 12/276968 | |
| DATED | : March 29, 2011 | |
| INVENTOR(S) | : Abbas Hassan et al. | |

It is certified that error appears in the above-identified patent and that said Letters Patent is hereby corrected as shown below:

On the Title page, Item (73), please replace "Synfuels International, Inc., Dallas, TX (US)" with "H R D Corporation, Houston, TX (US)" as shown below:

(73) Assignee: ~~Synfuels International, Inc., Dallas, TX (US)~~ H R D Corporation, Houston, TX (US)

Signed and Sealed this
Fourteenth Day of August, 2012

David J. Kappos
*Director of the United States Patent and Trademark Office*